United States Patent
Skelnik et al.

(10) Patent No.: US 9,612,110 B2
(45) Date of Patent: Apr. 4, 2017

(54) OBSERVATION DEVICE OF CORNEA FOR TRANSPLANTATION, AND AUXILIARY LIGHT SOURCE UNIT USED FOR THE SAME

(71) Applicant: KONAN MEDICAL, INC., Nishinomiya-shi (JP)

(72) Inventors: Debra Skelnik, Nishinomiya (JP); Yoichi Hamada, Nishinomiya (JP)

(73) Assignee: KONAN MEDICAL, INC., Nishinomiya-Shi, Hyogo (JP)

( * ) Notice: Subject to any disclaimer, the term of this patent is extended or adjusted under 35 U.S.C. 154(b) by 69 days.

(21) Appl. No.: 14/457,448

(22) Filed: Aug. 12, 2014

(65) Prior Publication Data
US 2015/0042956 A1   Feb. 12, 2015

(30) Foreign Application Priority Data
Aug. 12, 2013 (JP) ................................ 2013-167277

(51) Int. Cl.
| | | |
|---|---|---|
| G01B 11/24 | (2006.01) | |
| A61F 2/14 | (2006.01) | |
| A01N 1/02 | (2006.01) | |

(52) U.S. Cl.
CPC ............ *G01B 11/24* (2013.01); *A01N 1/0263* (2013.01); *A61F 2/142* (2013.01)

(58) Field of Classification Search
CPC .... A61B 3/0008; A61B 3/107; A01N 1/0242; A61F 2/14; A61F 2/141–2/142; G02B 21/0012

USPC ........ 351/221, 245–247, 216–218, 205–206, 351/212; 623/5.11–5.12, 5.14; 435/304.1
See application file for complete search history.

(56) References Cited

U.S. PATENT DOCUMENTS

| | | | |
|---|---|---|---|
| 5,956,123 A | 9/1999 | Abe et al. | |
| 2005/0213037 A1 | 9/2005 | Abdullayev et al. | |
| 2006/0209256 A1* | 9/2006 | Beyerlein | A61B 3/103 351/205 |

FOREIGN PATENT DOCUMENTS

JP       3922486 B2    5/2007

* cited by examiner

*Primary Examiner* — Scott J Sugarman
*Assistant Examiner* — Ibrahima Diedhiou
(74) *Attorney, Agent, or Firm* — Knobbe Martens Olson & Bear LLP

(57) ABSTRACT

An observation device includes: a holding board that holds an observation container accommodating a cornea for transplantation to be observed; a specular reflection optical system including an illumination optical system and an imaging optical system, which include a light source and an imaging unit, for observing the cornea for transplantation; and an auxiliary light source that illuminates the cornea for transplantation from the back and has an auxiliary illumination optical axis inclined with respect to an observation base axis that divides in half an intersecting angle of the illumination optical axis of the illumination optical system and an imaging optical axis of the imaging optical system, wherein the auxiliary light source is installed in a freely pivoting manner about a predetermined rotation axis so that a relative inclination angle with respect to the observation base axis of the auxiliary illumination optical axis can be continuously changed.

3 Claims, 12 Drawing Sheets

(a)

(b)

(a)

(b)

(a) OLD (b) NEW (a) OLD (b) NEW

OBSERVATION DEVICE OF CORNEA FOR TRANSPLANTATION, AND AUXILIARY LIGHT SOURCE UNIT USED FOR THE SAME

BACKGROUND OF THE INVENTION

Field of the Invention

The present invention relates to an observation device of a cornea for transplantation, and an auxiliary light source unit used for the same.

Description of the Related Art

In the ophthalmic treatment for corneal transplantation, a special observation device that can observe, photograph, or measure an area of a cornea cell, a cell density, a state, a thickness of a cornea for transplantation, and the like for safe and suitable transplantation of the cornea has been conventionally developed. For such observation device, a microscope in which an observation container, which accommodates the cornea for transplantation to be observed, is mounted on a holding board, and observed using a specular reflection method is used (see e.g., patent document 1).

A configuration including a light source for applying light from the back surface of the cornea apart from the light source of the microscope when observing the existence of corneal abnormality with the microscope is disclosed (see patent document 2).

PRIOR ART DOCUMENT

Patent Document

Patent Document 1: JP-B-3922486
Patent Document 2: US 2005/0213037 A

SUMMARY OF THE INVENTION

FIG. 1 is a schematic view describing a method of measuring the thickness of a cornea for transplantation using an observation device adopting the specular reflection method. A cornea 20 for transplantation is accommodated in an observation container 30 with a predetermined liquid, and mounted on a predetermined location on the observation device. The cornea 20 for transplantation has a configuration including an endothelium 22, an epithelium 23, and a substantial layer 24 sandwiched between the endothelium 22 and the epithelium 23, where the thickness of the cornea 20 for transplantation is measured with the thickness between the endothelium 22 and the epithelium 23.

The specular reflection method is a method of diagonally irradiating the cornea 20 for transplantation with slit light 31 formed by a light source and a slit (not shown), and observing the cornea using the fact that specular reflection light from the surface of the cornea 20 for transplantation is reflected at the same angle as an incident angle of the observation light. An observation point 35 is a focusing position where a slit image obtained by the slit light 31 is imaged by an objective lens 34L, and position adjustment by the observation device is carried out such that the endothelium 22 to be observed is positioned at the observation point 35, as shown in FIG. 1A. Specular reflection light 32 from the endothelium 22 is re-imaged at an imaging unit 11 with an objective lens 34R, so that the picture of the endothelium 22 can be checked with a monitor.

When desiring to measure the thickness of the cornea 20 for transplantation, the observation device is moved in a direction approaching an optical system so that the observation point 35 is at the position of the surface of the epithelium 23. In other words, after focusing on the endothelium 22 as shown in FIG. 1A, the observation device is moved while the picture in the imaging unit 11 is checked. Thus, if a specular reflection image (slit image) by specular reflection light 33 from the epithelium 23 is confirmed at the imaging unit 11, determination can be made that the observation point 35 coincides with the surface of the epithelium 23. Therefore, the thickness of the cornea can be measured based on a movement distance of the observation device from the state of FIG. 1A.

However, the specular reflection image sometimes cannot be checked at the imaging unit 11 with the above procedure. The reason resides in the cornea 20 for transplantation in which the specular reflection light from the epithelium 23 does not exist or is very few. Therefore, whether or not the epithelium 23 is positioned at the observation point 35 cannot be known as in FIG. 1B, and the thickness of the cornea 20 for transplantation consequently cannot be measured.

Such event may occur by the state of the cornea 20 for transplantation provided from the donor, the storage state, and the like, but the cause is not definite. However, the state of the cornea 20 for transplantation provided from each donor normally differs for each donor, and thus it is preferable that the image of the epithelium when the observation point 35 is coincided at the position of the epithelium 23 can be checked at the imaging unit 11 in the cornea 20 for transplantation provided from any donor.

In light of the foregoing, the inventors of the present application contrived a method for observing the epithelium by applying light from the back of the cornea. Although the configuration of including backlight for applying light from the back of the cornea is disclosed in patent document 2 described above, such backlight is provided for the purpose of observing defects in the cornea by observing wrinkles, scars, and the like in a wider range of a cornea strip, and is not provided to image the epithelium.

Furthermore, even if the backlight of patent document 2 is applied for the observation of the epithelium, the following problems arise. In other words, when illuminating the cornea from the back, the illuminating direction needs to be appropriately set. For example, if direct light transmitted through the cornea for transplantation enters the imaging unit via an imaging optical system, the observation of the epithelium becomes difficult due to flare. The backlight of patent document 2 has a very high degree of freedom in position adjustment, and thus the task of finding the appropriate illuminating direction is cumbersome and troublesome.

In view of the above problems, it is an object of the present invention to provide an observation device of a cornea for transplantation that can easily measure the thickness of the cornea regardless of the state of the cornea for transplantation, and an auxiliary light source unit to be used in the observation device.

An observation device of a cornea for transplantation according to the present invention includes a holding board that holds an observation container accommodating a cornea for transplantation to be observed;

a specular reflection optical system including an illumination optical system and an imaging optical system, which include a light source and an imaging unit, for observing the cornea for transplantation through a specular reflection method; and at least one auxiliary light source, which illuminates the cornea for transplantation from back and which has an auxiliary illumination optical axis inclined with respect to an observation base axis that divides in half an intersecting angle of an illumination optical axis of the illumination optical system and an imaging optical axis of the imaging optical system; wherein the auxiliary light source is installed in a freely changing manner so that a relative inclination angle with respect to the observation base axis of the auxiliary illumination optical axis is continuously or intermittently changed.

According to such configuration, at least one auxiliary light source (backlight) for illuminating the cornea for transplantation from the back is arranged separate from the light source of the specular reflection optical system. The auxiliary light source is different from the light source of the specular reflection optical system, and applies from the back of the cornea facing the imaging optical system to generate the scatter refracted light at the epithelium. In the case of the specular reflection optical system, the existence of the endothelium can be checked with the image within the slit illumination range, but when observing the epithelium without specular reflection light, the specular reflection image cannot be observed and the epithelium cannot be found.

Thus, the auxiliary light source is applied so that the refracted scattered light of the epithelium can be captured at the imaging unit without limiting to the region within the slit. The epithelium can be focused on the observation point while the refracted scattered light is checked with the monitor.

In the case of the present invention, the auxiliary light source is installed in a freely changing manner so that the auxiliary illumination optical axis of the auxiliary light source is inclined with respect to the observation base axis of the specular reflection optical axis, and the relative inclination angle can be continuously or intermittently changed. Therefore, the appropriate position, where a flare image is not generated, can be searched while the auxiliary light source moves. Furthermore, the procedure can be avoided from becoming cumbersome since the operation is a simple operation of moving operating the auxiliary light source. As a result, the observation device of the cornea for transplantation that can easily measure the thickness of the cornea can be provided.

Specifically, the observation device of the cornea for transplantation according to the present invention further preferably includes a housing installed on the holding board, wherein the at least one auxiliary light source is installed in the housing, and the housing is fitted to the holding board to be freely pivotable.

According to the configuration, the housing, in which the auxiliary light source is installed, is attached in a freely pivoting manner with respect to the holding board. Therefore, the auxiliary light source is also freely pivotable. The auxiliary illumination optical axis of the auxiliary light source can be set to an appropriate state through a simple operation of pivot operating the housing.

More specifically, the observation device of the cornea for transplantation according to the present invention further preferably includes a housing mounted on the holding board to interiorly accommodate the observation container, the housing including a cylindrical main body, an opening formed at one end side of the cylindrical main body, and a top plate portion formed at the other end side of the cylindrical main body; wherein the auxiliary light source is installed on the top plate portion, and the opening is fitted to the holding board so that the housing is freely pivotable about a cylindrical axis of the cylindrical main body.

According to such configuration, the auxiliary light source is installed on the top plate portion of the housing. The housing has a cylindrical main body, and the opening on one end side is fitted to the holding board. Thus, similar to the description made above, the auxiliary illumination optical axis of the auxiliary light source can beset to an appropriate state through a simple operation of pivot operating the housing.

The observation device of the cornea for transplantation according to the present invention further preferably includes a housing installed on the holding board, wherein the at least one auxiliary light source is installed in the housing, and the auxiliary light source is installed in the housing so as to be freely pivotable about a predetermined axis center.

According to such configuration, the auxiliary illumination optical axis of the auxiliary light source can be set to an appropriate state through a simple operation of pivoting the auxiliary light source.

Furthermore, the observation device of the cornea for transplantation according to the present invention further preferably includes a housing installed on the holding board, wherein a plurality of the auxiliary light sources are installed in the housing, each of the auxiliary light sources is installed so that a relative inclination angle with respect to the observation base axis differs from each other, and any one of the auxiliary light sources is selectable.

According to such configuration, check can be made by selecting and operating any one of the auxiliary light sources, and hence the auxiliary illumination optical axis of the auxiliary light source can be set to an appropriate state through a simple operation, similarly.

Furthermore, the observation device of the cornea for transplantation according to the present invention further preferably includes a light source holding body installed on the holding board, at least one auxiliary light source being installed in the light source holding body, and the light source holding body being moved to continuously or intermittently change the relative inclination angle.

According to such configuration, the auxiliary illumination optical axis of the auxiliary light source can be set to an appropriate state by moving the light source holding body. The movement of the light source holding body includes, for example, up and down direction, rotating direction, and the like.

The auxiliary light source unit according to the present invention is used in the observation device of the cornea for transplantation, and includes at least an auxiliary light source of the present invention, and a housing of the present invention.

The operations and the effects by the above configuration are as described above, and hence the thickness of the cornea can be easily measured. Furthermore, the provision as an option can be realized by unitizing. Furthermore, a cap shape can be realized, thus facilitating the attachment and detachment to and from the holding board.

DETAILED DESCRIPTION OF THE PREFERRED EMBODIMENTS

Figure 1:
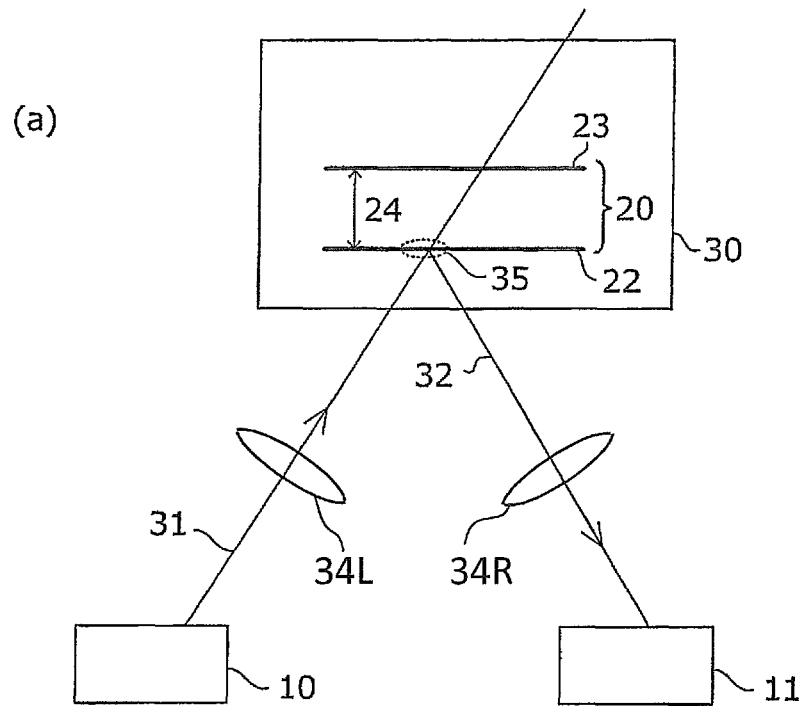
FIG. 1A and FIG. 1B are schematic views describing a method for measuring a thickness of a cornea for transplantation.
Figure 1:
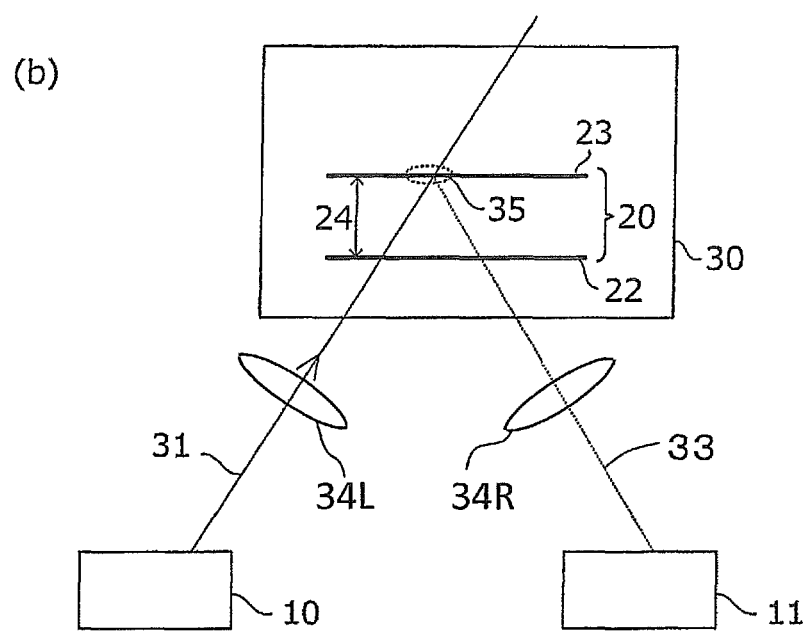

Embodiments of an observation device of a cornea for transplantation of the present invention will be described with reference to the drawings. In each figure, the dimensional ratio of the drawing may not necessarily match the actual dimensional ratio.

[Device Configuration]

Figure 2:
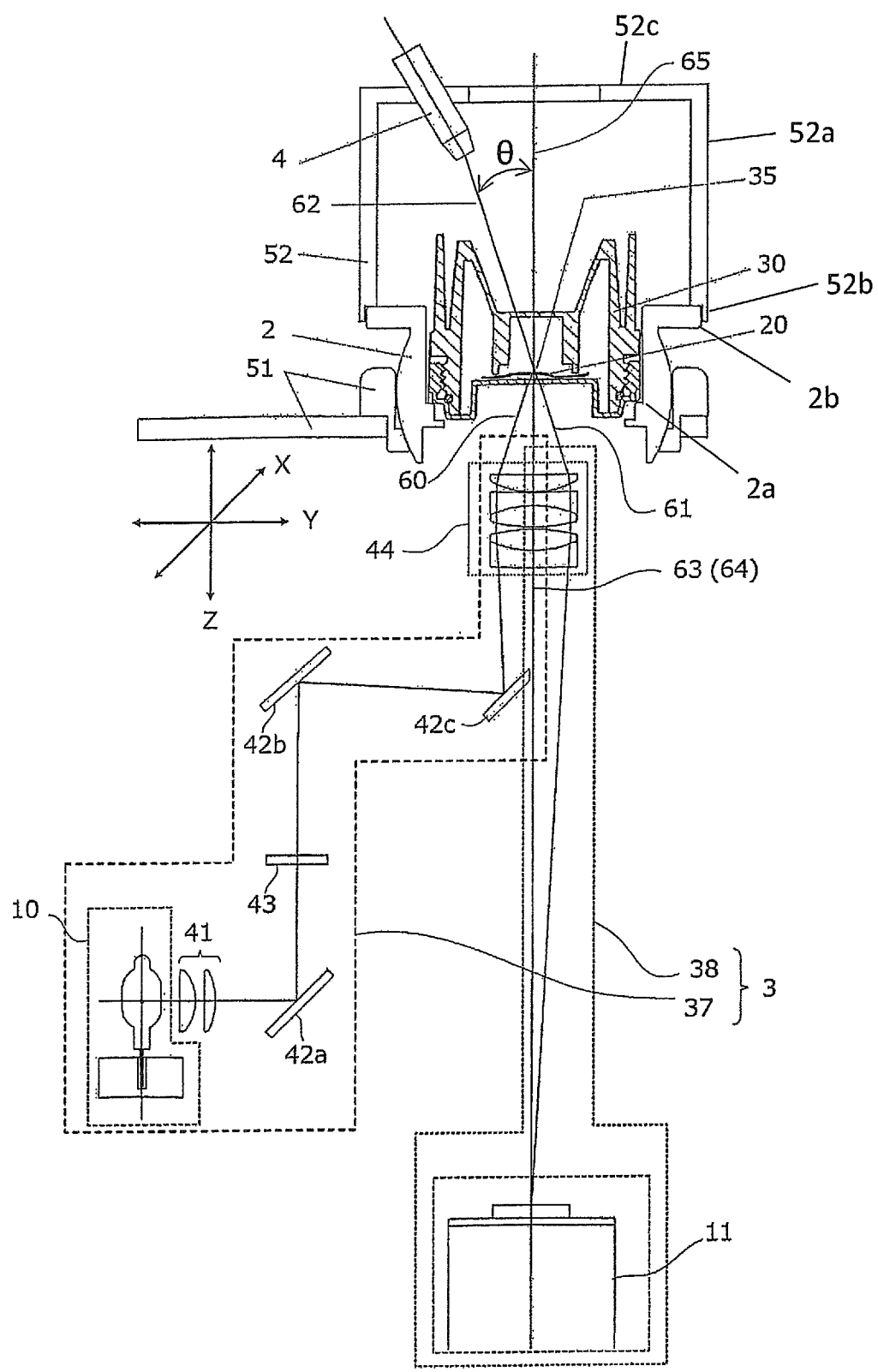
FIG. 2 is a schematic view showing one example of a configuration of an observation device of the cornea for transplantation.

FIG. 2 is a schematic view showing one example of a configuration of the observation device of the cornea for transplantation of the present invention. The observation device 1 includes a holding board 2, a specular reflection optical system 3, and an auxiliary light source 4.

The specular reflection optical system 3 includes an illumination optical system 37 and an imaging optical system 38. The illumination optical system 37 includes a light source 10, a condenser lens 41, mirrors 42a, 42b, 42c, a slit 43, and an objective lens system 44. The imaging optical system 38 includes the objective lens system 44 and an imaging unit 11. The imaging unit 11 is configured with a CCD camera, and the like, and is able to perform image observation with a monitor (not shown). In the observation device 1 shown in FIG. 2, the objective lens system 44 of the illumination optical system 37 and the objective lens system 44 of the imaging optical system 38 are commonly used for the objective lens system 44, so that miniaturization of the specular reflection optical system 3 is realized. The arrangement method and the number of mirrors, the number of condenser lenses, and the like can be appropriately changed.

A halogen lamp, an LED, and the like can be used for the light source 10. The light from the light source 10 is passed through the slit 43, and enters a predetermined observation point 35 in the cornea 20 for transplantation through the objective lens system 44. The light ray of the slit light passes through a position (left half in the objective lens system 44 in FIG. 2) shifted in one direction from an optical axis 63 of the objective lens system 44 when passing through the objective lens system 44, and enters the cornea 20 for transplantation as a light flux having an effective illumination optical axis 60 at a small incident angle from a direction slightly inclined with respect to the optical axis 63 of the objective lens system 44. The slit light is specular reflected in a symmetric direction with respect to the optical axis 63 of the objective lens system in the cornea 20 for transplantation. The specular reflected light (reflected image of cornea 20 for transplantation) enters the objective lens system 44, and passes through a position (right half in the objective lens system 44 in FIG. 2) symmetric with the slit light with respect to the optical axis 63 of the objective lens system in the objective lens system 44, that is, is imaged on the imaging unit 11 as a light flux having an effective imaging optical axis 61.

That is, the specular reflection optical system 3 is configured so that the position of intersection of the effective illumination optical axis 60 and the effective imaging optical axis 61 configures the observation point 35, and a slit image obtained by the slit light is imaged at the observation point. Therefore, it is important to position the cornea for transplantation, which is the observing target, at the observation point.

In the present specification, an axis that divides in half an intersecting angle of the effective illumination optical axis 60 and the effective imaging optical axis 61 is defined as an "observation base axis 64". In the present embodiment, the objective lens system 44 is arranged so that the optical axis 63 of the objective lens system 44 coincides with the observation base axis 64. Both axes are desirably exactly coincided, but the arrangement in which the axes are slightly shifted is not to be excluded from the present invention.

The holding board 2 is a board for holding the observation container 30 that accommodates the cornea 20 for transplantation, and holds the observation container 30 at a predetermined location in a mounted state. The holding board 2 is opened so as not to inhibit the optical path of the specular reflection optical system 3. The observation container 30 is a container for accommodating the cornea 20 for transplantation, and for example, the cornea 20 for transplantation is accommodated therein by way of a predetermined liquid such as a medicinal solution. The observation container 30 has a substantially cylindrical shape, by way of example, and can be mounted on a mounting surface 2a arranged in the holding board 2.

A supporting board 51 has a configuration of being movable frontward and backward, leftward and rightward, and upward and downward (three-axes directions of XYZ) with respect to the observation base axis 64 by an adjustment mechanism (not shown). With the arrangement of such adjustment mechanism, the setting of the observation position of the cornea and the position adjustment of the cornea to the observation point (focusing position) are carried out. An example of the adjustment mechanism includes a screw feeding slidably moving mechanism.

The supporting board 51 is a board having a female-type spherical surface, and the holding board 2 is a board having a male-type spherical surface, so that the holding board 2 is made freely inclinable with respect to the supporting board 51 by fitting the holding board 2 and the supporting board 51 through a spherical surface. A more satisfactory specular reflection on the cornea 20 for transplantation can be searched by inclining the holding board 2. When the supporting board 51 is moved in the three-axes directions with the holding board 2 incorporated in the supporting board 51, the holding board 2 is also moved in the same direction integrally with the supporting board 51.

A specific mode in which the holding board 2 and the supporting board 51 are fitted is not limited to the above shape as long as the holding board 2 is supported in a freely inclining manner.

<Auxiliary Light Source Unit>

The observation device 1 includes an auxiliary light source unit mounted on the holding board 2. The auxiliary light source unit includes a housing 52, and furthermore, the housing 52 is configured by a cylindrical main body 52*a*, an opening 52*b* formed at one end side of the cylindrical main body 52*a*, and a top plate portion 52*c* formed at the other end side of the cylindrical main body 52*a*. The opening 52*b* of the housing 52 is fitted to a fit-in surface 2*b* of the holding board 2. The housing 52 is thus attached to the holding board 2 in a freely pivoting manner. The rotation axis becomes a cylindrical axis of the cylindrical main body 52*a*.

An elongate cylindrical auxiliary light source 4 is attached to the top plate portion 52*c* with the axis inclined. The shape of the auxiliary light source 4 is not limited to above.

The housing 52 has a cap shape overall, and is mounted on the holding board 2 so as to interiorly accommodate the observation container 30. The housing 52 may be configured with a material having low translucency to eliminate the influence of disturbance light such as room illumination, solar light, and the like. The specific shape of the housing 52 is not limited to FIG. 2.

According to the above configuration, the auxiliary light source 4 is also integrally pivot operated by pivot operating the housing 52 with respect to the holding board 2. The housing 52 is merely mounted on the holding board 2, so that the attachment/detachment operation is also simples.

The cylindrical axis 65 of the housing 52 is arranged to coincide with the observation base axis 64. The axis centers are preferably exactly coincided, but may be slightly shifted. Further, when the holding board 2 is used in a tilted manner, the cylindrical axis 65 may be in a tilted state.

The auxiliary light source 4 has an auxiliary illumination optical axis 62 inclined with respect to the observation base axis 64, and is configured to illuminate the cornea 20 for transplantation from the back of the specular reflection optical system 3. As shown in FIG. 2, the auxiliary illumination optical axis 62 is defined as a line (or a plane) connecting the light source 4 and the cornea 20 for transplantation that is to be observed. As described above, the relative inclination angle $\theta$ of the auxiliary illumination optical axis 62 with respect to the observation base axis 64 can be continuously changed by pivoting the housing 52 about the cylindrical axis 65. The relative inclination angle $\theta$ is defined as an angle formed by the auxiliary illumination optical axis 62 and the observation base axis 64. Further, even if an absolute value of the angle $\theta$ does not change, the relative inclination angle $\theta$ is defined as to change in cases where a direction of the auxiliary illumination optical axis 62 changes. The above definition is applied to all the other embodiments.

<Thickness Measuring Procedure>

A method of measuring the thickness of the cornea 20 for transplantation using the observation device 1 will now be described with reference to an image imaged by the imaging unit 11 shown in FIG. 3A to FIG. 3D. Such images are images obtained when a dummy cornea is used for the cornea 20 for transplantation, but will be described as the cornea 20 for transplantation.

First, the observation container 30 accommodating the cornea 20 for transplantation is installed on the holding board 2. The light source 10 is then lighted to apply slit light, so that specular reflection light (slit image) is received by the imaging unit 11. The supporting board 51 is moved in the XY direction by an adjustment mechanism (not shown) to select a target observation area, in this case, the endothelium 22 of a predetermined area of the cornea 20 for transplantation.

Figure 3A:
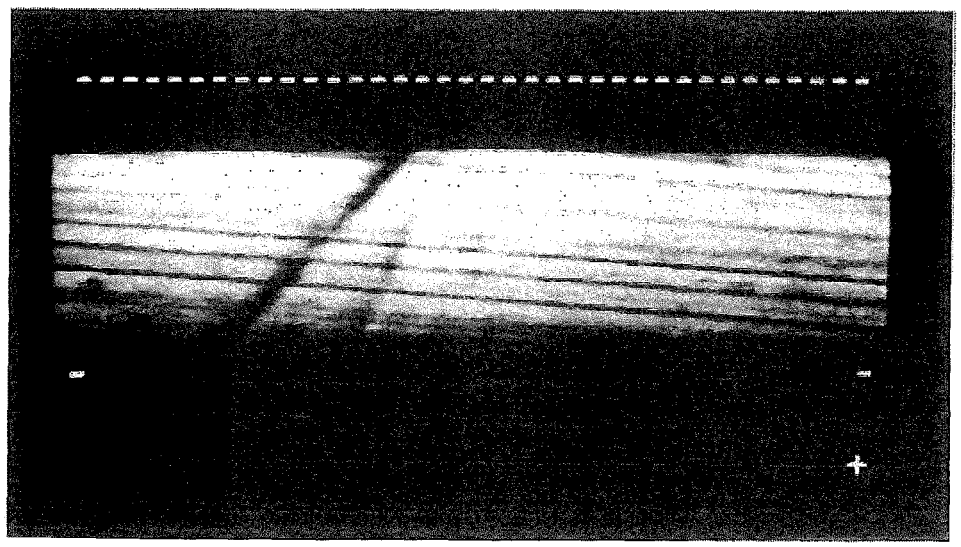
FIG. 3A is an example of an image imaged by an imaging unit using a dummy cornea.

The supporting board 51 is then moved in the Z direction to be adjusted so that the endothelium 22 reaches the observation point 35 (focusing position) (see FIG. 1). FIG. 3A is an example of an image in which the specular reflection light 32 in the endothelium 22 is re-imaged at the imaging unit 11. A specular reflection image 81 by the slit light can be checked at the imaging unit 11.

An operation of inclining the holding board 2 to obtain a more satisfactory specular reflection image may be carried out. In this case, the XYZ adjustment by the adjustment mechanism needs to be carried out again.

Thus, the housing 52 of the auxiliary light source unit is installed on the holding board 2 and the auxiliary light source 4 attached to the housing 52 is lighted under a state in which the specular reflection image of the endothelium 22 can be checked at the imaging unit 11. The housing 52 is pivoted about the cylindrical axis 65, that is, the observation base axis 64 to adjust the auxiliary light source 4 to a position suited for observation.

Figure 3B:
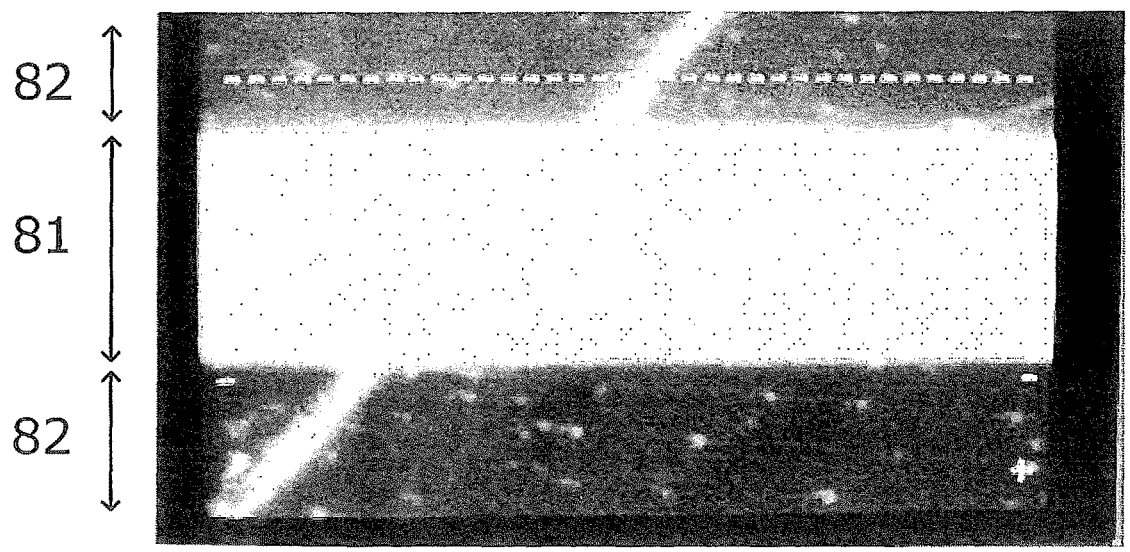
FIG. 3B is an example of an image imaged by the imaging unit using the dummy cornea.

When the auxiliary light source 4 is lighted, the imaging unit 11 has a possibility of receiving the following three types of light. The first light is the specular reflection light of the slit light from the light source 10 at the surface of the cornea 20 for transplantation. The second light is the light in which the light from the auxiliary light source 4 is scatter reflected and refracted at the surface of the cornea 20 for transplantation, and enters an optical path of the imaging optical system 38. The third light is light in which the light from the auxiliary light source 4 is transmitted through the cornea 20 for transplantation and enters the optical path of the imaging optical system 38 as is. The position suited for observation is the position where the third light is weak and the second light is strong with respect to the light received by the imaging unit 11. If the third light is too strong, the image of the imaging unit 11 becomes white overall, and the image of the second light to be used at the time of focusing on the epithelium 23 side cannot be checked. The housing 52 is pivoted to adjust to such suited position. FIG. 3B is an example of the imaged image of the imaging unit 11 after the adjustment is completed.

Compared with FIG. 3A, the light receiving amount at the imaging unit 11 is slightly increased with the auxiliary light source 4 being lighted, and thus the region of the specular reflection image 81 by the slit light is whitened, and the image 82 by the scattered refracted light is displayed at the position on the outer side thereof. In the image of FIG. 3A, only the light (slit light) from the light source 10 is applied, and hence only the specular reflection image 81 by such slit light is confirmed, and the image is not confirmed on the outer side. The image 82 by the scatter refracted light also exists in the region of the specular reflection image 81 under normal conditions, but such region cannot be visualized because the region is saturated white.

The supporting board 51 is then moved in the Z direction by the adjustment mechanism (not shown). More specifically, the supporting board 51 is moved in the direction approaching the optical system 3. In this case, the specular reflection image 81 and the image 82 by the scatter refracted light displayed at the time point of FIG. 3B start to be defocused. The specular reflection image 81 moves on the screen of the imaging unit 11 in the defocused state, and hence the defocusing amount becomes large and eventually, the image cannot be checked on the screen.

Figure 3C:
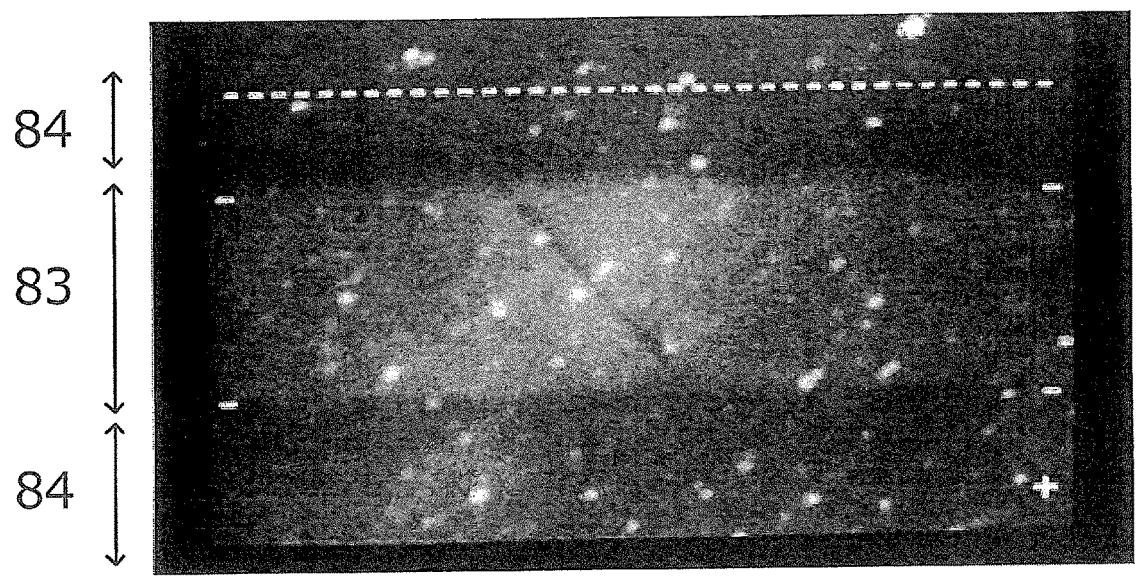
FIG. 3C is an example of an image imaged by the imaging unit using the dummy cornea.

Furthermore, when the supporting board 51 continues to be moved in the Z direction, a specular reflection image 83 by the slit light may again be displayed in a darker state than the specular reflection image 81 which is displayed at the time point of FIG. 3B, in some cases (see FIG. 3C). This corresponds to the specular reflection image 83 at the position of the epithelium 23. In this case, an image 84 by the scatter refracted light at the position of the epithelium 23 is also displayed on the screen in the focused state.

Actually, after the auxiliary light source 4 is lighted, the specular reflection image 83 by the slit light may not be visualized on the screen in the imaging unit 11 even if the supporting board 51 is moved in the Z direction. In this case, adjustment is made to the focusing position based on the image obtained by the scatter refracted light 84 displayed on the screen. Such image is the image obtained by the scatter refracted light 84 at the surface of the epithelium 23, and the surface of the epithelium 23 can be coincided with the observation point 35.

The thickness of the cornea 20 for transplantation thus can be measured based on the movement amount in the Z direction of the supporting board 51 from the state of FIG. 3B to the state of FIG. 3C.

Figure 3D:
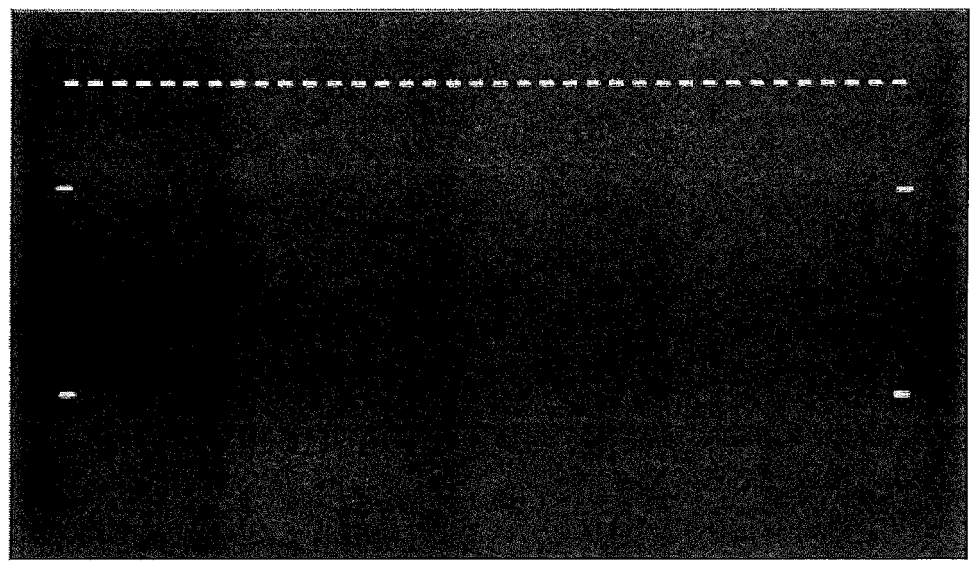
FIG. 3D is an example of an image imaged by the imaging unit using the dummy cornea.

FIG. 3D shows an imaged image of the imaging unit 11 when the supporting board 51 is moved in the Z direction by the movement amount of the same extent as the state of FIG. 3C without lighting the auxiliary light source 4 from the state of FIG. 3A. In FIG. 3D, the image obtained by the specular reflection light of the epithelium 23 and the image obtained by the scatter refracted light as shown in FIG. 3C are not displayed at all. Thus, whether the epithelium 23 is positioned on the observation point 35 cannot be determined by checking only such screen, and thus the thickness of the cornea 20 for transplantation cannot be measured.

Figure 4:
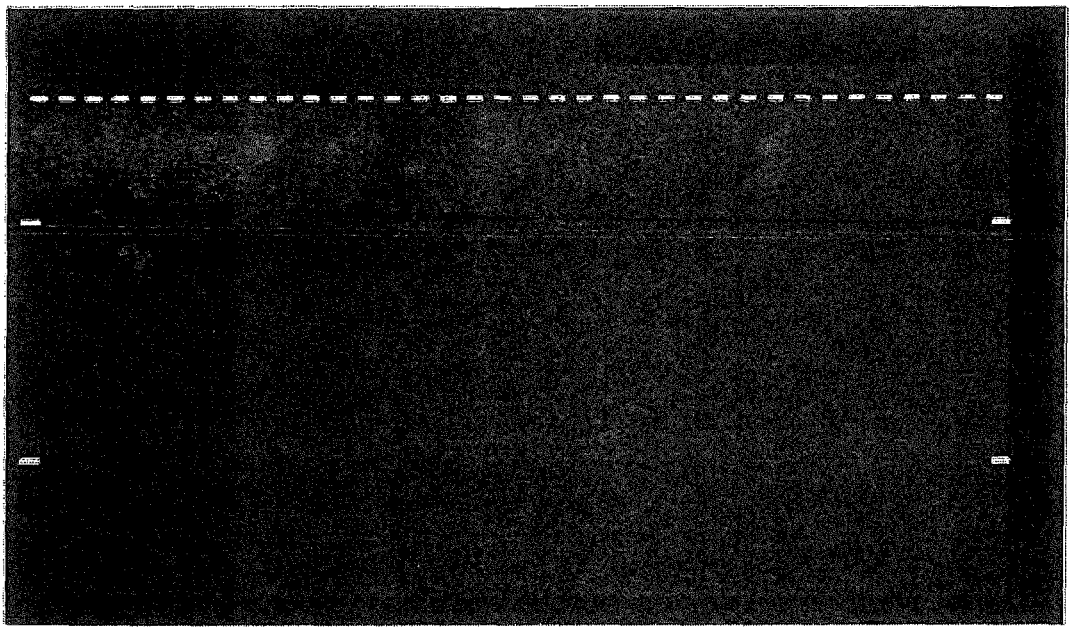
FIG. 4A and FIG. 4B are examples of images imaged by the imaging unit using a cornea for transplantation provided from a donor.
Figure 4:
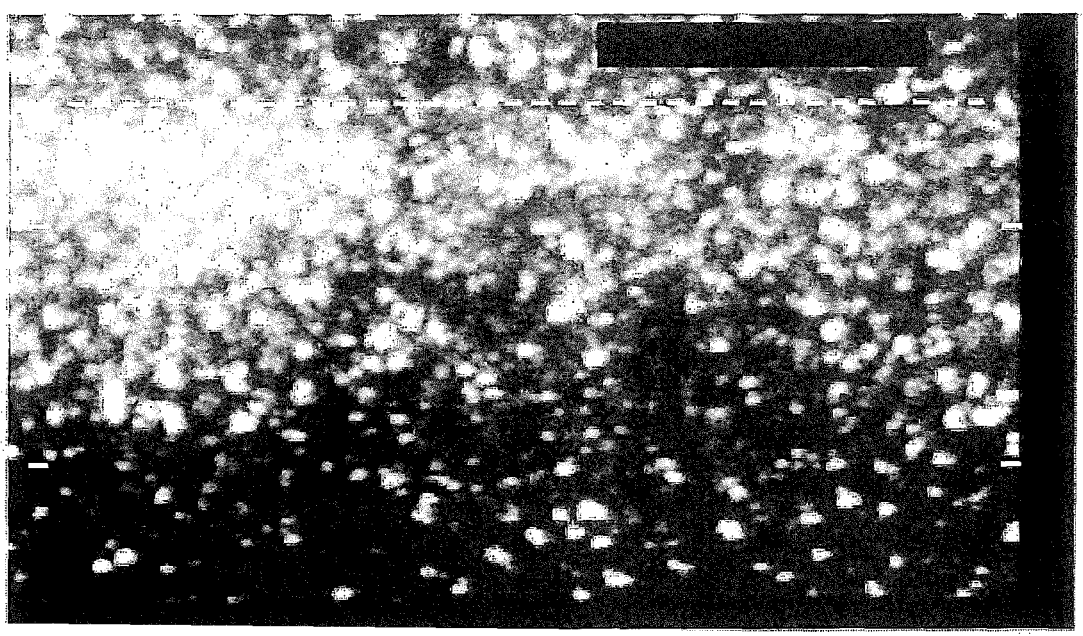

FIG. 4 shows an imaged image in the imaging unit 11 when the cornea 20 for transplantation provided from the actual donor is accommodated in the observation container 30 and observed by the observation device 1, and in either case, adjustment is carried out so that the epithelium 23 is positioned on the observation point 35. FIG. 4A corresponds to a case in which the auxiliary light source 4 is not lighted, FIG. 4B corresponds to a case in which the auxiliary light source 4 is lighted.

In FIG. 4A, the image obtained by the specular reflection light and the image obtained by the scatter refracted light of the epithelium 23 are not displayed at all, similar to FIG. 3D, and thus whether or not the epithelium 23 is positioned on the observation point 35 cannot be recognized from only the image. On the contrary, in FIG. 4B, although the image obtained by the specular reflection light is difficult to recognize clearly, the image obtained by the scatter refracted light can be checked, and thus focusing can be carried out while looking at the image and the epithelium 23 can be positioned on the observation point 35. According to FIG. 4, even if the actual cornea 20 for transplantation is used, at least the image of the scatter refracted light at the position of the epithelium 23 can be visualized in the imaging unit 11 by the lighting of the auxiliary light source 4.

In the method described above, an housing 52 is installed and the auxiliary light source 4 is lighted after the focusing operation of the endothelium 22, but the housing 52 may be attached to the holding board in advance.

In the embodiment described above, an example in which one auxiliary light source is arranged has been described, but a plurality of auxiliary light sources may be arranged. The shape of the housing is not limited to the shape of the present embodiment, and various shapes may be adopted.

<Auxiliary Light Source Unit According to Another Embodiment>

Figure 5:
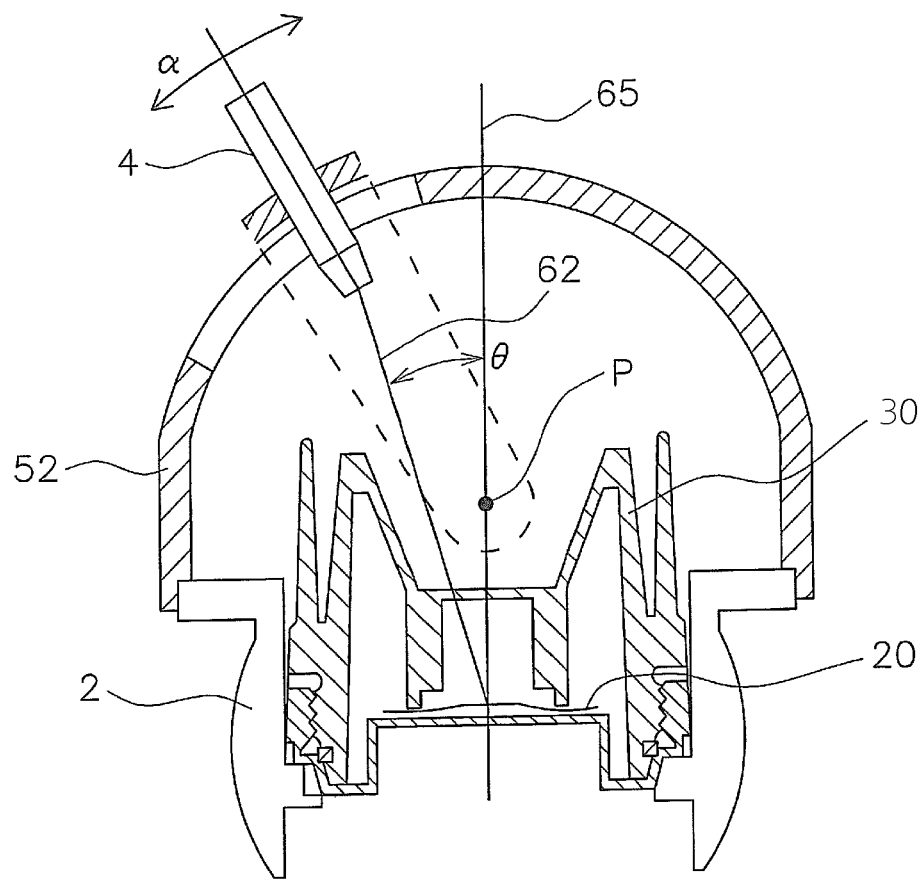
FIG. 5 is a view showing a configuration of an auxiliary light source unit according to a second embodiment.

An auxiliary light source unit according to a second embodiment will now be described with FIG. 5. In the present embodiment, the auxiliary light source 4 can be pivoted about the center of rotation P set on the axis center 65, as shown with an arrow α. Thus, the relative inclination angle θ with respect to the observation base axis 64 can be continuously changed. The upper surface of the housing 52 is a hemispherical surface, and is supported by an arm (not shown) so that the auxiliary light source 4 can be moved along such hemispherical surface.

Figure 6:
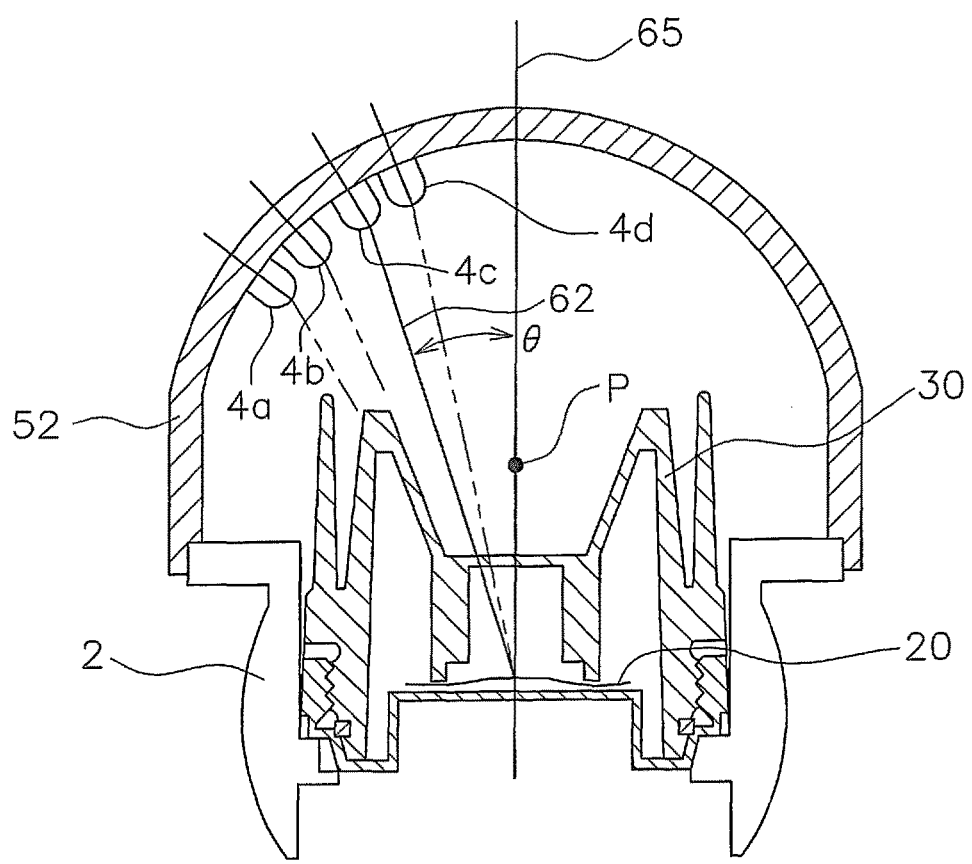
FIG. 6 is a view showing a configuration of an auxiliary light source unit according to a third embodiment.

FIG. 6 shows the auxiliary light source unit according to a third embodiment. In the present embodiment, four LEDs 4a to 4d are installed on the back of the hemispherical top surface of the housing 52. The optical axes of each of LEDs 4a to 4d are set to intersect with each other at point P set on the axis center 65. One of the LEDs 4a to 4d is selected and applied, so that the relative inclination angle θ with respect to the observation base axis 64 can be intermittently changed. The number of LEDs can be appropriately changed. The light source may not be the LED.

In the second and third embodiments, the housing 52 may be pivoted or may not be pivoted about the axis center 65. If the housing 52 can be pivoted, the illuminating direction can be changed not only for the longitude direction but also for the latitude direction.

The first light (specular reflection light), the second light (scatter reflection/refracted light by auxiliary light source), and the third light (direct light from the auxiliary light source) when the auxiliary light source 4 areas described above. When adjusting the position of the auxiliary light source 4, it is important that the third light becomes small and the second light becomes large.

When the housing 52 is pivoted, the light receiving amount of the third light greatly changes. In the second and third embodiments, when the optical axis of the auxiliary light source 4 is changed, the change in the third light is small, and the appearance of the cornea by the second light changes. Thus, if the housing 52 is made to be pivotable, the position where the third light appears weak and the second light appears strong is searched by pivoting the housing 52. The application direction of the auxiliary light source 4 is changed in such state, so that the appropriate state of the auxiliary light source 4 can be easily searched. The appearance of the cornea by the second light is changed while the change in the third light small is suppressed, so that the observation can be easily carried out when looking at the wrinkles, scars, and the like of the cornea. This is useful when observing the degree of scar of the cornea by the cornea refractive surgical procedure, and the like.

If the housing 52 cannot be pivoted, the appropriate application direction of the auxiliary light source 4 is to be set while looking at the light amount balance of the second light and the third light.

A plurality of light sources arranged to a ring shape around the axis center 65 may be used for the light source. For example, in the case of the third embodiment shown in FIG. 6, four ring-shaped light source groups having different diameters of the ring are installed, and one of the ring-shaped light sources is selected.

Figure 7:
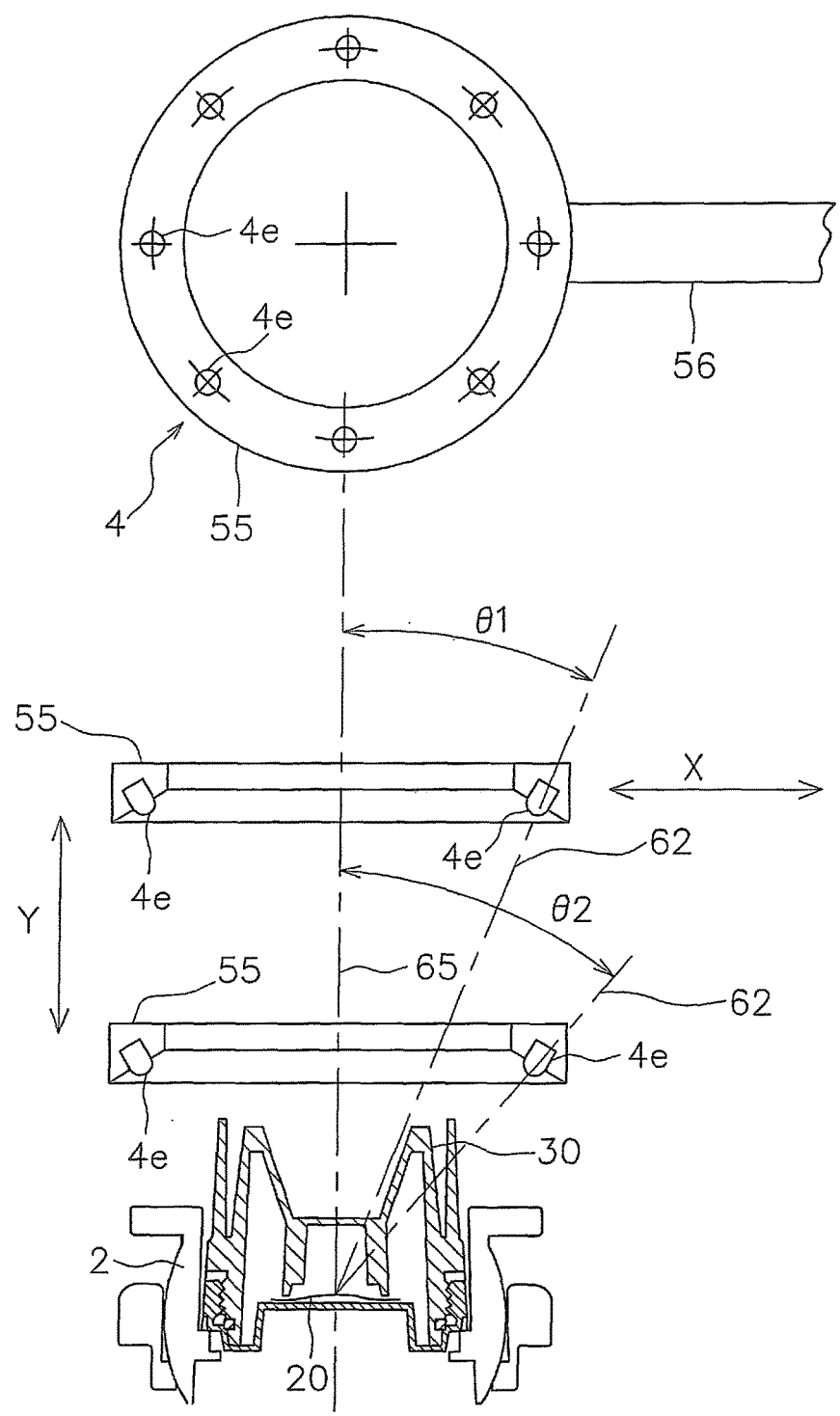
FIG. 7 is a view showing a configuration of an auxiliary light source unit according to a fourth embodiment.

The auxiliary light source unit according to a fourth embodiment will now be described with reference to FIG. 7. The auxiliary light source 4 includes eight LEDs 4e. These LEDs 4a are arranged at equal interval along the circumferential direction. The LED 4*a* is held by a ring-shaped light source holding body 55. The number of LEDs 4*a* can be appropriately determined. A light source such as a lamp, and the like other than the LED may be used.

The light source holding body 55 is coupled to an arm 56 which has the other end attached to a main body side (not shown). The arm 56 is preferably configured with a flexible material, but is not limited to a specific structure.

The auxiliary light source 4 can be moved in the horizontal direction (X) and the vertical direction (Y). The auxiliary light source 4 can be inserted and removed with respect to the observation container 30 by being moved in the horizontal direction. A different moving method such as a flip-up method, and the like can be adopted instead of the horizontal movement.

The auxiliary light source 4 is moved in the vertical direction while being installed on the observation container 30, so that the relative inclination angle (θ1, θ2) with respect to the observation base axis of the auxiliary illumination optical axis can be continuously or intermittently changed.

The light source holding body 55 is formed to a ring-shape for the following reasons. The light source holding body 55 is prevented from making contact with the observation container 30 when moved to the lower side, to obtain a large angle θ2. Furthermore, the observation container 30 can be viewed from the upper side if formed to a ring-shape. Moreover, a case of using a vial container for the observation container 30 can be responded. The vial container may have a non-transparent lid and long, and thus can be observed if formed to a ring shape. The position of the light source can be lowered by inserting the light source holding body 55 from above the vial container by being formed to a ring shape.

Rather than lighting all of the plurality of LEDs (light sources) 4*e*, the LEDs may be selectively lighted.

<Comparative Example of Photographed Image>

Figure 8:
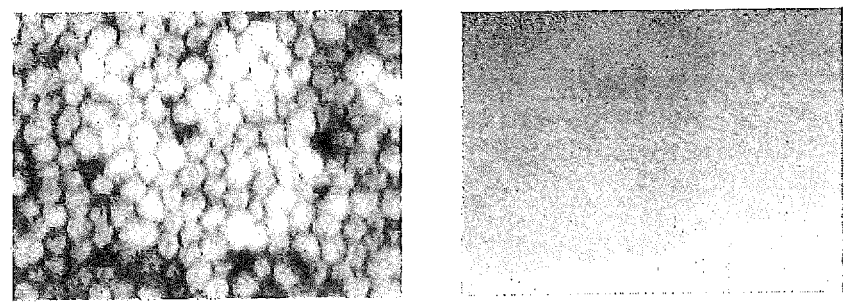
FIG. 8A and FIG. 8B show a first comparative example of a photographed image in which the auxiliary light source unit according to the present invention is used and a conventional photographed image in which the auxiliary light source unit is not used.
Figure 8:
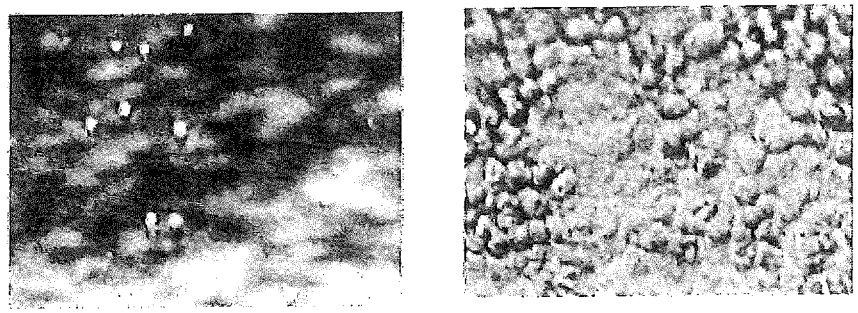

Next, a comparative example of a photographed image in which the auxiliary light source unit of the present invention is used, and a conventional photographed image in which the auxiliary light source unit is not used is shown in FIG. 8. FIG. 8A shows the photographed image in which the auxiliary light source unit is not used, where the left side shows the endothelium image and the right side shows the epithelium image. FIG. 8B shows the photographed image in which the auxiliary light source unit is used, where the left side shows the endothelium image and the right side shows the epithelium image. In particular, the epithelium image becomes a clear image by using the auxiliary light source unit. The details of the bumps and the attachment of the endothelium and epithelium surfaces can be clearly observed by using the auxiliary light source unit.

Figure 9:
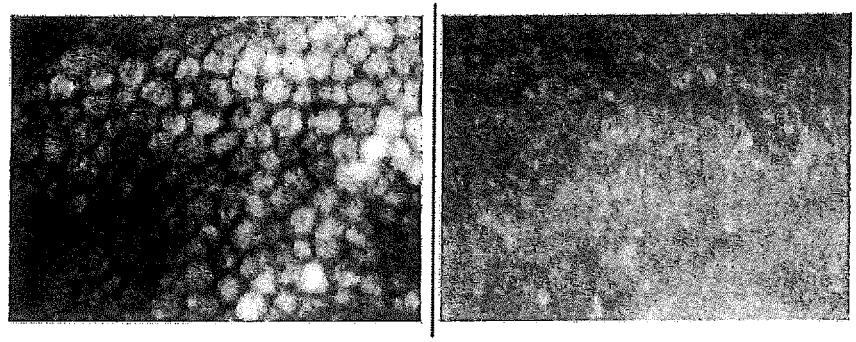
FIG. 9A and FIG. 9B show a second comparative example of a photographed image in which the auxiliary light source unit according to the present invention is used and a conventional photographed image in which the auxiliary light source unit is not used.
Figure 9:
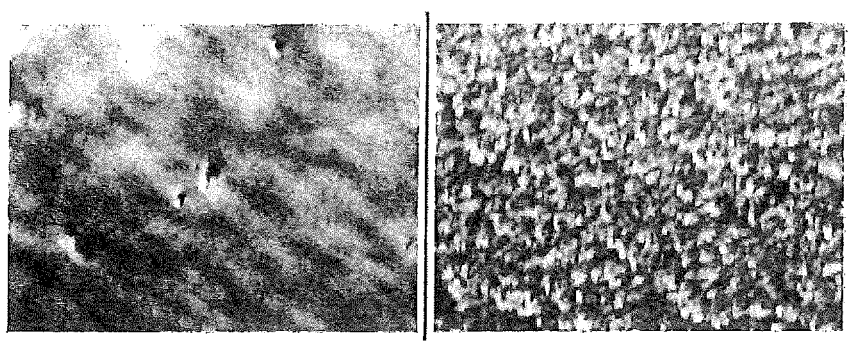

FIG. 9 is an example of another photographed image. FIG. 9A shows the photographed image in which the auxiliary light source unit is not used, where the left side shows the endothelium image and the right side shows the epithelium image. FIG. 9B shows the photographed image in which the auxiliary light source unit is used, where the left side shows the endothelium image and the right side shows the epithelium image. Similar to the case of FIG. 8, a clear image is obtained by using the auxiliary light source unit. Similar to the case of FIG. 8A and FIG. 8B, the details of the bumps and the attachment of the endothelium and epithelium surfaces can be clearly observed by using the auxiliary light source unit.

The effects of the auxiliary light source unit according to the present invention can also be checked from such photographed image examples.

What is claimed is:

1. An observation device of a cornea for trans plantation comprising:
    a holding board that holds an observation container accommodating a cornea for transplantation to be observed;
    a specular reflection optical system including an illumination optical system and an imaging optical system, which include a light source and an imaging unit, for observing the cornea for transplantation through a specular reflection method;
    at least one auxiliary light source, which illuminates the cornea for transplantation from a side opposite to the side on which the specular reflection optical system observes the cornea for transplantation and which has an auxiliary illumination optical axis inclined with respect to an observation base axis that divides in half an intersecting angle of an illumination optical axis of the illumination optical system and an imaging optical axis of the imaging optical system; and
    a housing installed on the holding board;
    wherein:
    the auxiliary light source is installed in a freely changing manner so that a relative inclination angle with respect to the observation base axis of the auxiliary illumination optical axis is continuously or intermittently changed, and
    the at least one auxiliary light source is installed in the housing, and the housing is fitted to the holding board to be freely pivotable.

2. The observation device of the cornea for transplantation according to claim 1, wherein the housing is mounted on the holding board to interiorly accommodate the observation container, the housing including a cylindrical main body, an opening formed at one end side of the cylindrical main body, and a top plate portion formed at the other end side of the cylindrical main body; wherein
    the at least one auxiliary light source is installed on the top plate portion, and the opening is fitted to the holding board so that the housing is freely pivotable about a cylindrical axis of the cylindrical main body.

3. An auxiliary light source unit used in an observation device of the cornea for transplantation comprising:
    an auxiliary illumination optical axis inclined with respect to an observation base axis that divides in half an intersecting angle of an illumination optical axis of an illumination optical system of the observation device and an imaging optical axis of an imaging optical system of the observation device, wherein the auxiliary light source is installed in a freely changing manner so that a relative inclination angle with respect to the observation base axis of the auxiliary illumination optical axis is continuously or intermittently changed; and
    a housing installed on a holding board of the observation device in which at one auxiliary light source is installed, wherein the housing is fitted to the holding board to be freely pivotable,
    wherein the auxiliary light source illuminates the cornea for transplantation from a side opposite to the side on which the illumination optical system and the imaging optical system observes the cornea for transplantation.

* * * * *